(12) United States Patent  
Ding (10) Patent No.: US 10,451,234 B2  
(45) Date of Patent: Oct. 22, 2019

(54) ELECTRONIC CANDLE

(71) Applicant: Nantong Ya Tai Candle Arts & Crafts Co., Ltd., Nantong, Jiangsu (CN)

(72) Inventor: Yingqi Ding, Nantong (CN)

(73) Assignee: NANTONG YA TAI CANDLE ARTS & CRAFTS CO., LTD., Nantong (CN)

( * ) Notice: Subject to any disclaimer, the term of this patent is extended or adjusted under 35 U.S.C. 154(b) by 86 days.

(21) Appl. No.: 15/679,158

(22) Filed: Aug. 17, 2017

(65) Prior Publication Data

US 2018/0283634 A1 Oct. 4, 2018

(30) Foreign Application Priority Data

Mar. 31, 2017 (CN) .......................... 2017 1 0209843  
Jun. 8, 2017 (CN) .......................... 2017 1 0426462

(51) Int. Cl.
| | |
|---|---|
| *F21S 10/04* | (2006.01) |
| *F21S 6/00* | (2006.01) |
| *H05B 33/08* | (2006.01) |
| *F21S 9/02* | (2006.01) |
| *A61L 9/12* | (2006.01) |
| *F21V 23/04* | (2006.01) |
| *H05B 37/02* | (2006.01) |
| *F21Y 115/10* | (2016.01) |

(52) U.S. Cl.
CPC .............. *F21S 10/043* (2013.01); *A61L 9/12* (2013.01); *A61L 9/122* (2013.01); *F21S 6/001* (2013.01); *F21S 9/02* (2013.01); *F21S 10/046* (2013.01); *F21V 23/04* (2013.01); *H05B 33/0845* (2013.01); *H05B 33/0857* (2013.01); *H05B 37/029* (2013.01); *A61L 2209/12* (2013.01); *F21Y 2115/10* (2016.08)

(58) Field of Classification Search
CPC .......... F21S 6/001; F21S 10/04; F21S 10/043; F21S 10/06  
See application file for complete search history.

(56) References Cited

U.S. PATENT DOCUMENTS

| | | | |
|---|---|---|---|
| 9,810,388 B1* | 11/2017 | Li | F21S 6/001 |
| 2009/0109663 A1* | 4/2009 | Tsai | F21S 6/001 |
| | | | 362/190 |
| 2011/0058363 A1* | 3/2011 | Fattizzi | F21L 4/02 |
| | | | 362/190 |
| 2015/0354769 A1* | 12/2015 | Patton | F21V 33/0052 |
| | | | 362/231 |
| 2016/0109083 A1* | 4/2016 | Li | F21S 10/046 |
| | | | 362/84 |
| 2016/0146414 A1* | 5/2016 | Dong | F21S 10/046 |
| | | | 362/232 |
| 2016/0290579 A1* | 10/2016 | Au | F21S 10/046 |

\* cited by examiner

*Primary Examiner* — Thien M Le  
*Assistant Examiner* — April A Taylor (57) ABSTRACT

An electronic candle is provided, wherein the electronic candle includes at least one lamp bead having at least two light emitting elements provided therein; the at least two light emitting elements change lights emitted therefrom to form a flickering effect. Using the electronic candle of this type, space utilization in the electronic candle is improved, and production cost is reduced.

8 Claims, 9 Drawing Sheets

ELECTRONIC CANDLE

CROSS REFERENCE TO RELATED APPLICATIONS

This application claims priority to Chinese Patent Applications No. 201710209843.6 filed on Mar. 31, 2017 and 201710428462.7 filed on Jun. 8, 2017, which are hereby incorporated by reference herein as if set forth in their entirety.

TECHNICAL FIELD

Embodiments of the present disclosure generally relate to electronic technology, and in particular relate to an electronic candle.

BACKGROUND

An electronic candle has features of being environmentally friendly, energy-saving, safe, convenient, and the like, and is becoming more and more popular with people.

At present, one lamp bead in an electronic candle generally emits light in a single color. A plurality of lamp beads are needed to emit lights in a variety of colors.

SUMMARY

The technical problem solved by the present disclosure is to provide an electronic candle, which is capable of improving space utilization in the electronic candle, and reducing production cost.

In order to solve the above technical problem, the present disclosure may provide an electronic candle, wherein the electronic candle includes at least one lamp bead having at least two light emitting elements provided therein; the at least two light emitting elements change lights emitted therefrom to form a flickering effect.

The present disclosure may achieve the following advantageous effects: by arranging at least two light emitting elements in one lamp bead, it is possible to save the inner space in the electronic candle, improve the space utilization, and reduce the production cost of the electronic candle.

DETAILED DESCRIPTION

Figure 1:
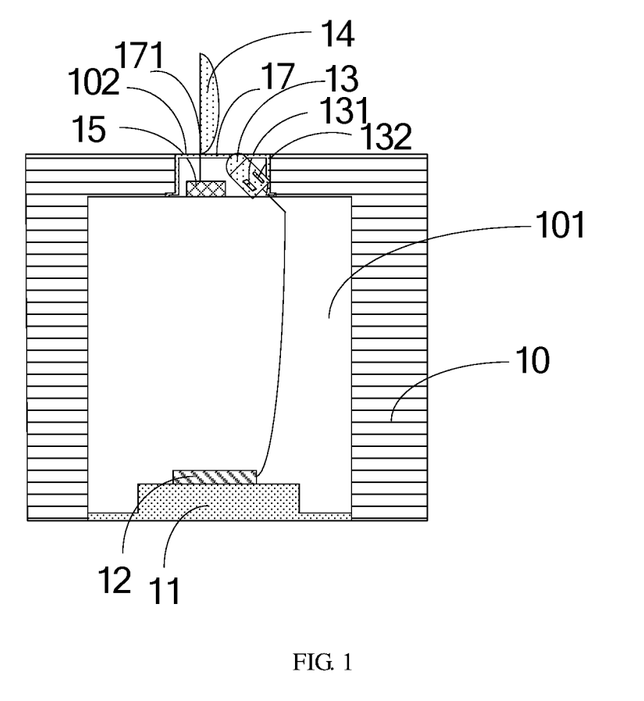
FIG. 1 is a frontal section view of a first embodiment of an electronic candle of the present disclosure.

Referring to FIG. 1, a frontal section view of a first embodiment of an electronic candle of the present disclosure is depicted in FIG. 1. The electronic candle may include a main body 10, a power supply 11, an electronic control device 12, a lamp bead 13, a flame head 14, and a fixed base 15.

A cavity 101 may be defined in the main body 101; the power supply 11 and the electronic control device 12 may be respectively fixed in the cavity 101. In this embodiment, the power supply 11 may be fixed on a bottom of the cavity 101, while the electronic control device 12 may be fixed on the power supply 11.

The flame head 14 may be fixed with respect to the lamp bead 13 via the fixed base 15 at an opening part 102 at the top of the main body 10. The flame head 14 may extend out of the main body 10 from the opening part 102. Optionally, for the convenience of assembly, it is possible to assemble the fixed base 15 and the lamp bead 13 in a housing 17. In this case, one end of the flame head 14 may be fixed on the fixed base 15, and the other end of the flame head 14 may extend out of the housing 17 via a top opening 171 of the housing 17. The housing 17 may be fixedly connected to the main body 10.

The lamp bead 13 may be arranged on one side of the flame head 14, and lights emitted from the lamp bead 13 may be irradiated onto the flame head 14. Of course, in other embodiments, it may also be possible for the lights emitted from the lamp bead 13 to be reflected to the flame head 14 via a reflector.

It is understood that, in this embodiment, one lamp bead is provided, which is the lamp bead 13. However, in other embodiments, two, three or more lamp beads may also be provided. Optionally, the lamp bead 13 may be in a same shape as an LED lamp; it may also possible for the lamp bead 13 to be in a shape of a circle, or in other shapes. The lamp bead 13 may include two light emitting elements 131 and 132. Of course, in other embodiments, more light emitting elements may be provided, and the quantity of the light emitting elements may be selected based on the design and production requirement. In this embodiment, the lamp bead comprising two light emitting elements are adopted for explanation.

Optionally, the light emitting element 131 and the light emitting element 132 may be light emitting diodes.

Figure 2:
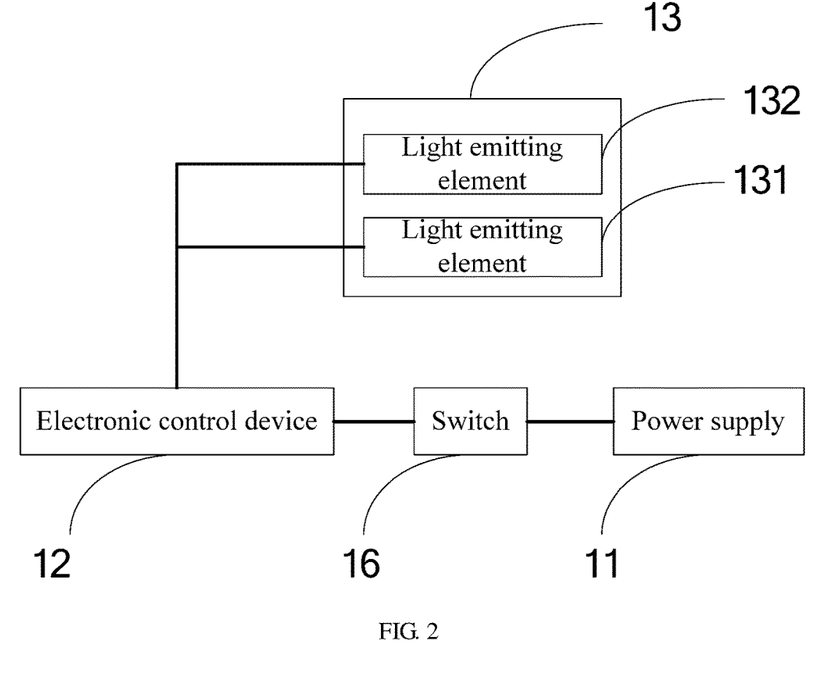
FIG. 2 is a circuit diagram of the first embodiment of the electronic candle of the present disclosure.

Referring to FIG. 2, a circuit diagram of the first embodiment of the electronic candle of the present disclosure is depicted in FIG. 2.

The power supply 11 may be configured to supply power to the whole electronic candle. Optionally, the power supply 11 may be a DC power. In one application case, the power supply 11 may be formed by one dry cell battery of 1.5V, or formed by a plurality of dry cell batteries of 1.5 V connected in series. In other application cases, the power supply 11 may also be formed by a button battery or batteries of other types.

The electronic control device 12 may be connected to the light emitting elements 131 and 132. Optionally, a driving chip (not shown here) may be arranged in the electronic control device 12, and may be configured to control the light emitting elements 131 and 132 to change lights emitted therefrom to form a flickering effect. In one application case, emission colors of the lights emitted from at least one of the two light emitting elements 131 and 132 may be changed, and thus a relative emission color or an overall color of the lights emitted from the two light emitting elements 131 and 132 may be changed. For example, the emission color of the light emitted from the light emitting element 131 may be changed over time, while the emission color of the light emitted from the light emitting element 132 remains unchanged; in this way, the relative emission color between the lights emitted from the light emitting elements 131 and 132 may be changed, and the overall color may also be changed. It may also be possible for the emission colors of lights emitted both by the light emitting elements 131 and 132 to be changed over time. In a further application case, emission strength of the lights emitted from at least one of the two light emitting elements 131 and 132 may be changed, and thus relative emission strength or overall strength of the lights emitted from the two light emitting elements 131 and 132 may be changed. For example, the emission strength of the light emitted from the light emitting element 131 may be changed over time, while the emission strength of the light emitted from the light emitting element 132 remains unchanged; in this way, the relative emission strength between the lights emitted from the light emitting elements 131 and 132 may be changed, and the overall strength may also be changed. It may also be possible for the emission strength of lights emitted both by the light emitting elements 131 and 132 to be changed over time. At this time, it is possible that when the light emitting element 131 emits light, the light emitting element 132 does not emit light; and when the light emitting element 131 does not emit light, the light emitting element 132 will emit light. That is, the light emitting element 131 and the light emitting element 132 may emit light alternately. It is understood that, in other embodiments, it may possible to use the electronic control device 12 to control the light emitting elements 131 and 132 to change the lights emitted therefrom to form a flickering effect, in connection with the emission color and emission strength based on the design requirements.

Figure 15:
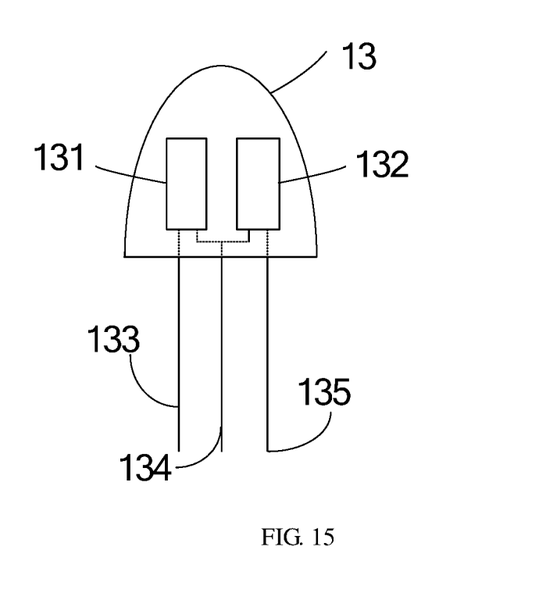
FIG. 15 is a schematic view of a lamp bead of the first embodiment of the electronic candle shown in FIG. 1 applied in one application case of the present disclosure.

Optionally, as is shown in FIG. 15, in order to reduce the quantity of pins of the lamp bead 13, in one application case of this embodiment, the light emitting element 131 and the light emitting element 132 may share at least one common lead wire to connect to the electronic control device 12. In the prior art, one light emitting element needs two lead wires including a positive wire and a negative wire for leading out, and thus two light emitting elements need four lead wires for leading out. However, in the embodiment of the present disclosure, it is possible for cathodes of at least two light emitting elements to be connected together, and one negative wire may be led out therefrom. For example, in the application case having the two light emitting elements 131 and 132, two positive wires and one negative wire may be led out therefrom. At this time, the lamp bead 13 has three pins including pins 133, 134 and 135 respectively. Correspondingly, the pins 133, 134 and 135 are respectively connected to three pins of the electronic control device 12, and thus the quantity of the lead wires may be reduced, and the quantity of the pins of the electronic control device 12 which are used may also be reduced as a result.

It is understood that, when the lamp bead 13 has N light emitting elements, in order to reduce the quantity of the pins of the lamp bead 13, the electrodes of the same polarity respectively of the N light emitting elements may be connected together. For example, the positive poles may be connected together, and one positive wire may be led out therefrom; while the negative wires of the light emitting elements each may be respectively led out. At this time, the lamp bead 13 may only have (N+1) pins, wherein N is a positive integer larger than or equal to 2. Referring to FIG. 2 again, optionally, in this embodiment, a switch 16 configured to control an on-off state of entire circuit may be further arranged between the power supply 11 and the electronic control device 12. Specifically, when the switch 16 is turned on, the light emitting elements 131 and 132 may change the lights emitted therefrom under the control of the electronic control device 12. However, when the switch 16 is turned off, the entire circuit is cut off, and thus the light emitting elements 131 and 132 do not emit light.

In the embodiments described above, at least two light emitting elements of the electronic candle may be arranged in the same lamp bead, thereby improving a space utilization of the electronic candle, saving material, and reducing production cost.

Figure 3:
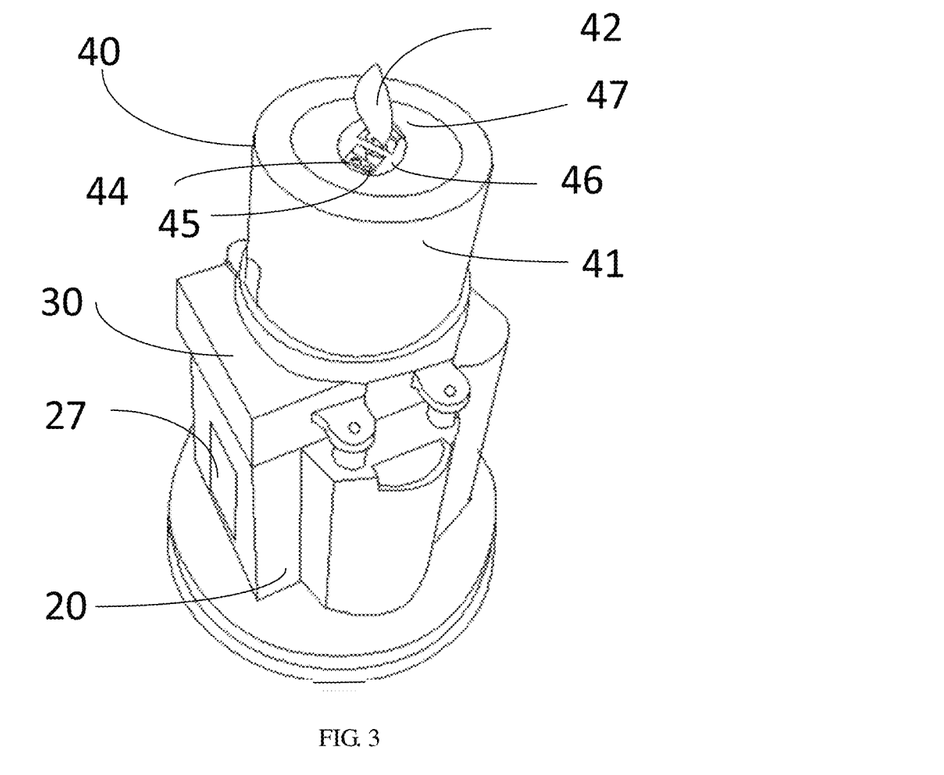
FIG. 3 is a view showing an internal structure of a main body of a second embodiment of an electronic candle of the present disclosure.

Referring to FIG. 3, a view showing an internal structure of a main body of a second embodiment of an electronic candle of the present disclosure is depicted in FIG. 3. A base 20, a fan assembly 30 and a lamp cap assembly 40 may be arranged inside the main body of the electronic candle.

Figure 4:
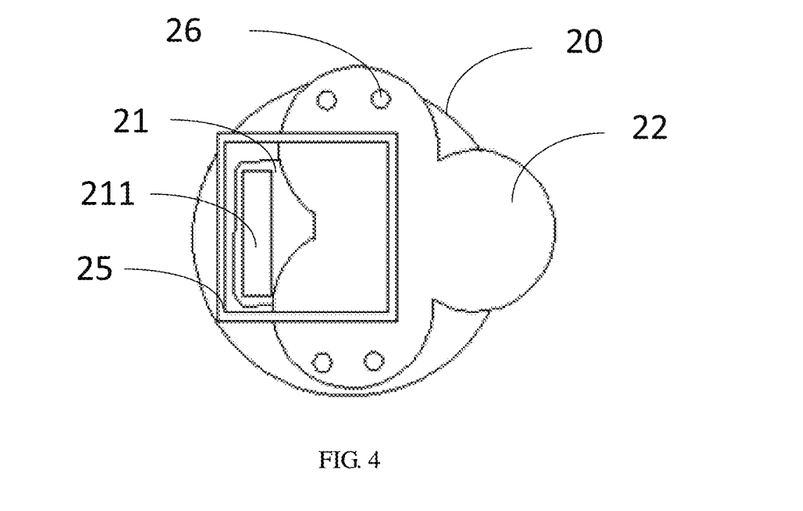
FIG. 4 is a top view of a base of the second embodiment of the electronic candle of the present disclosure.
Figure 5:
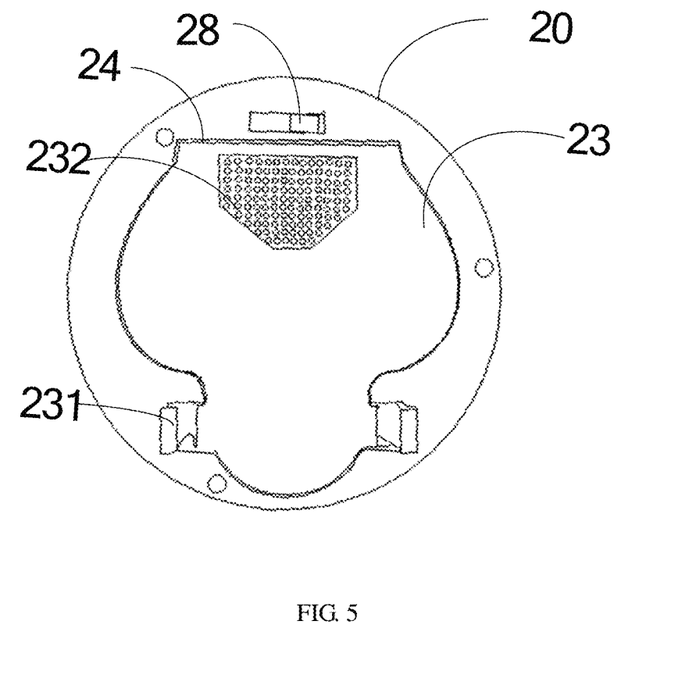
FIG. 5 is a bottom view of a base of the second embodiment of the electronic candle of the present disclosure.

Referring to FIG. 4 and FIG. 5, the base 20 may include a bottom cover plate 23, and a fragrance cavity 21 and a power supply cavity 22 are defined in the base 20.

The power supply cavity 22 may be arranged on one side of the fragrance cavity 21. A power supply configured to supply power to the electronic candle for the operation thereof may be arranged in the power supply cavity 22. Optionally, in this embodiment, the power supply cavity 22 may be in a shape having three circles crossed with each other. A fragrance element 211 may be arranged in the fragrance cavity 21. A stepped surface 24 recessed downwardly may be formed on a bottom surface of the base 20 corresponding to the fragrance cavity 21 and the power supply cavity 22. The bottom cover plate 23 may be embedded into the stepped surface 24, and may be engaged with the bottom surface of the base 20 via a buckle 231. Meanwhile, at least one hole 232 may be defined in a position on the bottom cover plate 23 that corresponds to the fragrance cavity 21. Fragrance of the fragrance element 211 in the fragrance cavity 21 may be diffused to the outer side of the electronic candle via the hole 232.

Meanwhile, a positioning frame 25 may be protruded from an upper surface of the base 20 that corresponds to an exit of the fragrance cavity 21. Optionally, in this embodiment, the positioning frame 25 may have a square cross-section, and a plurality of positioning posts 26 may be arranged on the upper surface of the base 20 on two sides of the positioning frame 25.

Figure 6:
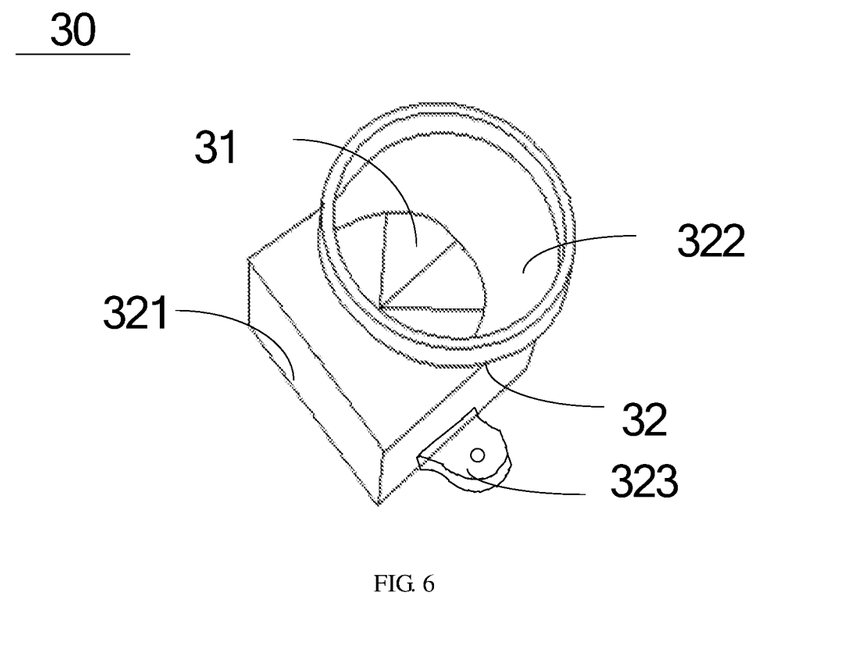
FIG. 6 is a structural view of a fan assembly of the second embodiment of the electronic candle of the present disclosure.

Referring to FIG. 6, the fan assembly 30 may include a fan 31 and a fan base 32.

A first cavity 321 and a second cavity 322 offset one another may be defined in the fan base 32, and a plurality of fixing lugs 323 may be arranged on an external wall of the first cavity 321. Optionally, in this embodiment, a cross-section of the first cavity 321 may be in shape of a square matching with the positioning frame 25. A cross-section of the second cavity 322 may be in shape of a circle. A dimension of the cross-section of the first cavity 321 may be larger than a dimension of the cross-section of the positioning frame 25. In this way, during the assembly process, the fan assembly 30 may be sleeved on an outer side of the positioning frame 25 via wall of the first cavity 321, and the fixing lugs 323 on two sides of the first cavity may be fastened to the positioning posts 26.

The fan 31 may be mounted in the first cavity 321, and an air exhausting surface of the fan 31 may be right opposite to the fragrance cavity 21. When the fan 31 rotates, fragrance of the fragrance element 211 in the fragrance cavity 21 may be diffused to the outer side of the electronic candle via the hole 232.

Figure 7:
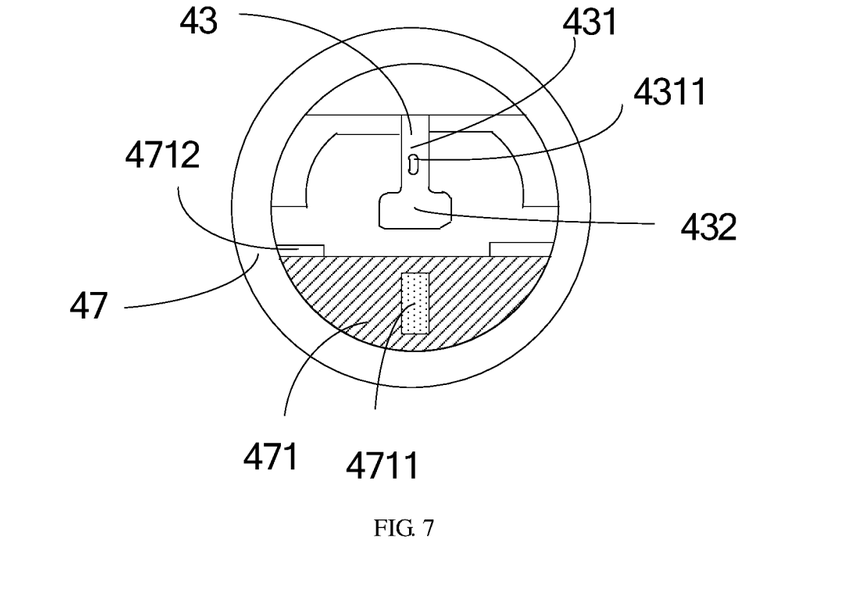
FIG. 7 is a top view of a flame head support of the second embodiment of the electronic candle of the present disclosure.

Referring to FIG. 3 and FIG. 7, the lamp cap assembly 40 may include a mounting base 41, a swingable flame head 42, a horizontal bar 43, a lamp holder 44, a lamp bead 45, a restricting ring 46 and a flame head support 47.

The lamp cap assembly 40 may be sleeved on an upper part of wall of the second cavity 322 of the fan base 32 via the mounting base 41. A receiving space may be defined in the mounting base 41, and the flame head support 47 may be received in the receiving space of the mounting base 41, and further fixedly connected to the mounting base 41.

Referring to FIG. 7, the horizontal bar 43 may be protruded from an inner wall of the flame head support 47. Optionally, in this embodiment, the horizontal bar 43 may be in shape of a "T", and may include a supporting portion 431 and a restricting portion 432. A recess 4311 may be further defined in the supporting portion 431. Optionally, in this embodiment, the recess 4311 may be arc-shaped. It is understood that, the horizontal bar 43 may be sleeved on and engaged with the inner wall of the flame head support 47 via a buckle. However, the horizontal bar 43 may also be integrated with the flame head support 47.

Figure 8:
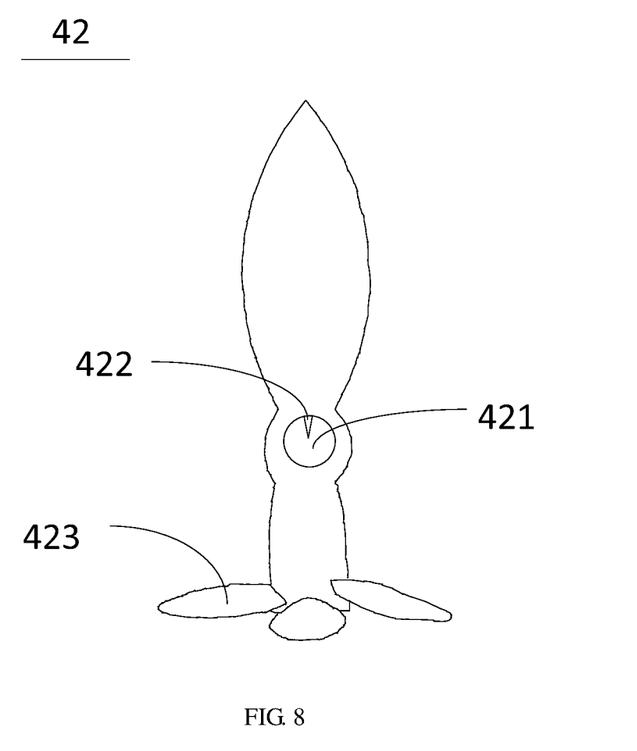
FIG. 8 is a structural view of a swingable flame head of the second embodiment of the electronic candle of the present disclosure.

Referring to FIG. 8, a horizontal through-hole 421 may be defined in the swingable flame head 42, and a support pin 422 may be protruded from a top portion of the horizontal through-hole 421. Specifically, the support pin 422 may be located in the center of gravity.

The swingable flame head 42 may pass through the horizontal bar 43 via the horizontal through-hole 421, and may be movably connected to the flame head support 47. Specifically, a width of the supporting portion 431 of the horizontal bar 43 may be smaller than a diameter of the horizontal through-hole 421, and a width of the restricting portion 432 may be larger than the diameter of the horizontal through-hole 421. During the assembly process, the swingable flame head 42 may be obliquely sleeved in the restricting portion 432 of the horizontal bar 43, and further entered the supporting portion 431 of the horizontal bar 43, and then supported in the recess 4311 via the support pin 422. The components of the swingable flame head 42 apart from the support pin 422 will not be in contact with the horizontal bar 43. When a breeze blows, the swingable flame head 42 may be supported in the recess 4311 using the support pin 422 as a supporting point, and thus the swingable flame head 42 may be swung freely and the swing portion of the swingable flame head 42 will be restricted in the recess 4311 all the time. Further, the swingable flame head 42 may not be stuck or shifted.

Optionally, in other embodiments, in order to ensure swinging effect of the swingable flame head 42, a blade 423 may be further arranged at a bottom of the swingable flame head 42. When the fan 31 is working, the breeze at the back of the fan 31 may cause the blade 423 to rotate, and in turn drive the swingable flame head 42 to swing.

It may be understood that, in other embodiments, the main body of the electronic candle may not contain the fan assembly 30. That is, the fragrance of the fragrance element 211 in the fragrance cavity 21 may be diffused to the outer side of the electronic candle via the hole 232. Alternatively or additionally, when the breeze blows, the swingable flame head 42 may swing in the effect of the breeze. When no fan assembly 30 is provided, the base 20 may be directly and fixedly connected to the lamp cap assembly 40. Specifically, the base 20 may be connected to the lamp cap assembly 40 using buckles, fixing lugs and fixing posts matching with each other, and the like.

Figure 9:
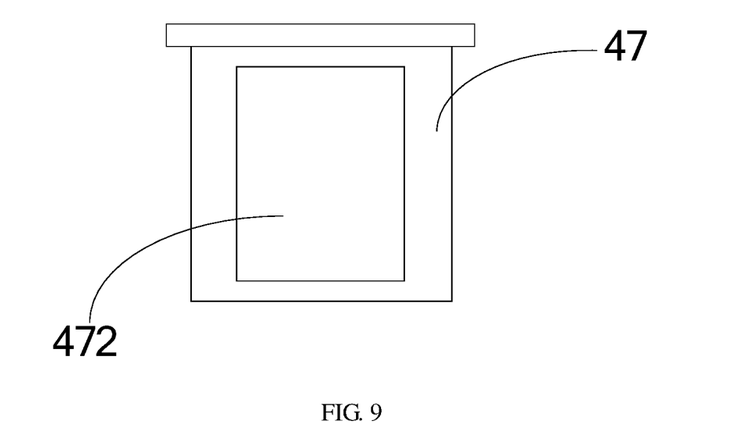
FIG. 9 is a side view of the flame head support of the second embodiment of the electronic candle of the present disclosure.

Referring to FIG. 7 and FIG. 9, an opening 472 may be defined on the inner wall of the flame head support 47 opposite to the horizontal bar 43, and a supporting plate 471 may be arranged on a bottom surface of the flame head support 47 that is adjacent to the opening 472. The lamp holder 44 may be embedded and further fixed into the supporting plate 471 of the flame head support 47 via the opening 472. Optionally, in other embodiments, the lamp holder 44 may be directly embedded in the inner wall of the flame head support 47 without passing through the opening 472.

Figure 10:
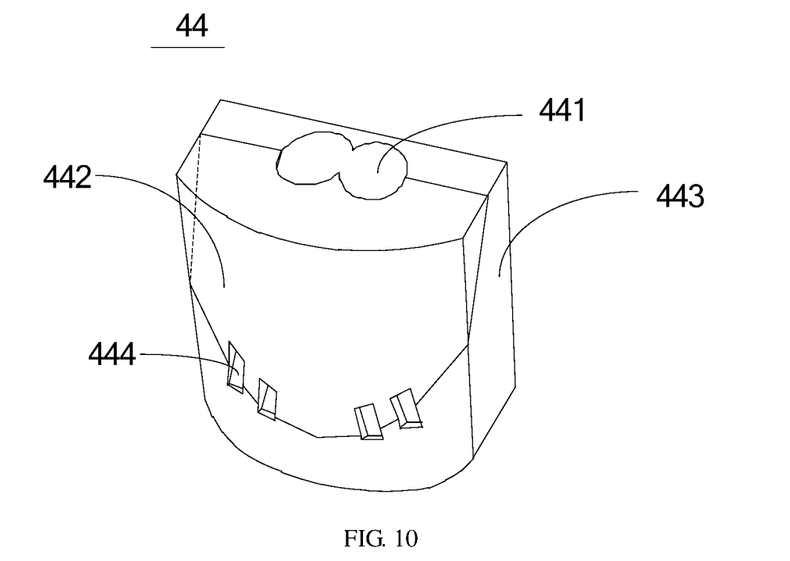
FIG. 10 is a structural view of a lamp holder of the second embodiment of the electronic candle of the present disclosure.

Referring to FIG. 10, at least one recessed part 441 may be formed in the lamp holder 44, and the lamp bead 45 may be mounted in the recessed part 441. In FIG. 10, two recessed parts 441 are illustrated for explanation; however, in other embodiments, one, three or more recessed parts 441 may be provided.

Figure 11:
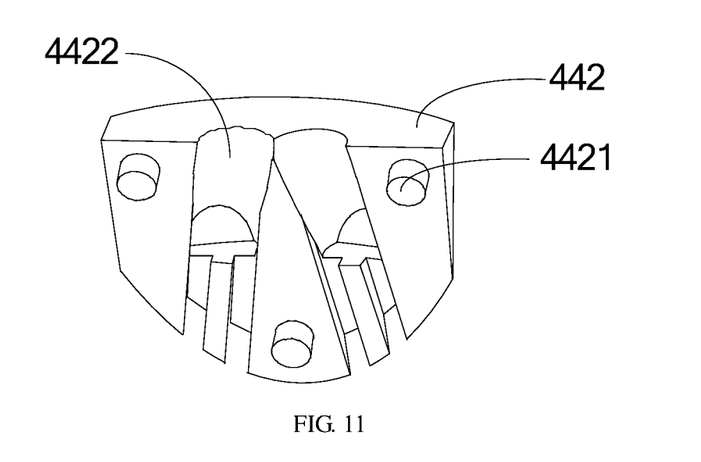
FIG. 11 is a structural view of a first section of the lamp holder shown in FIG. 10.
Figure 12:
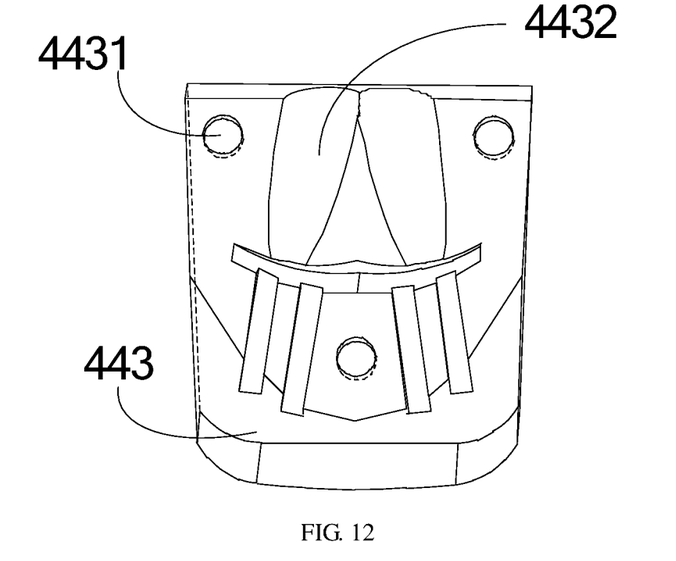
FIG. 12 is a structural view of a second section of the lamp holder shown in FIG. 10.

For the convenience of assembling and replacing a new lamp bead, the lamp holder 44 in this embodiment may include two portions including a first portion 442 and a second portion 443. Referring to FIG. 11 and FIG. 12, at least one locking post 4421 may be arranged on the first portion 442, while at least one locking hole 4431 matching with the at least one locking post 4421 may be formed in the second portion 443. Meanwhile, a first receiving space 4422 may be defined in the first portion 442, while a second receiving space 4432 may be defined in the second portion 443. After the first portion 442 and the second portion 443 are locked together via the locking post 4421 and the locking hole 4431, a third receiving space may be formed by the first receiving space 4422 and the second receiving space 4432. The third receiving space is the recessed part 441. During the assembly process, it is possible to place the lamp bead 45 in the first receiving space 4422 of the first portion 442, and then lock the second portion 443 and the first portion 442 together, meanwhile the pins of the lamp bead 45 may extend out via a lead wire hole 444. It is understood that, during the assembly process, it may also possible to place the lamp bead 45 in the second receiving space 4432 of the second portion 443, and then lock the first portion 442 and the second portion 443 together.

Figure 13:
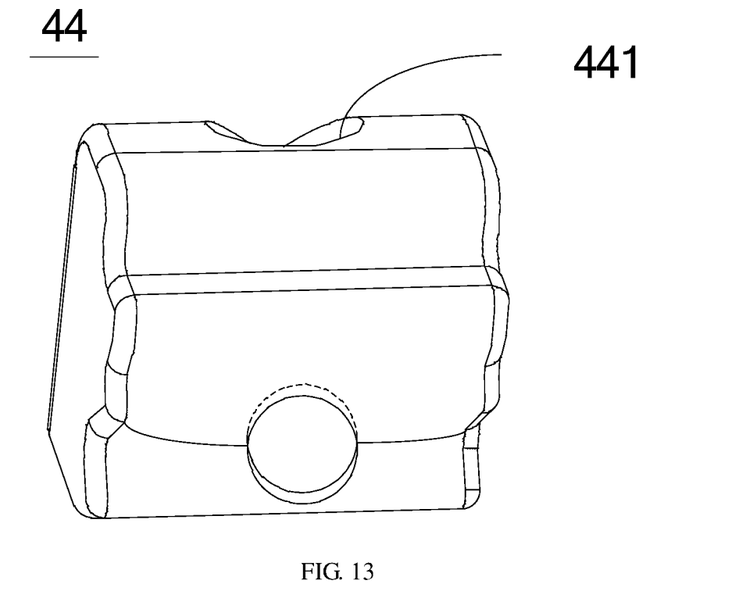
FIG. 13 is a structural view of a lamp holder of a further embodiment of the electronic candle of the present disclosure.

It is understood that, in other embodiments, the lamp holder 44 may be in one-piece or unitarily formed, as is shown in FIG. 13. In FIG. 13, one recessed part 441 is provided. However, it is understood that two or more recessed parts 441 may be provided in other embodiments.

It is also understood that the shape of the lamp holder 44 will not be specifically limited, and may be designed based on the requirements of beauty and production.

Meanwhile, in order to ensure that the position of the lamp holder 44 will not displace after the lamp holder 44 is embedded into the flame head support 47, a notch 4711 and a baffle 4712 may be further arranged on the supporting plate 471. Correspondingly, a protrusion (not shown here) matching with the notch 4711 may be further protruded from a surface of the lamp holder 44 that is in contact with the supporting plate 471. After the lamp holder 44 is embedded into the flame head support 47, the lamp holder 44 may be closely socketed into the flame head support 47.

Meanwhile, after the lamp holder 44 is embedded into the flame head support 47, the lamp bead 45 is located on one side of the swingable flame head 42, and the lights emitted from the lamp bead 45 may be irradiated onto the swingable flame head 42. Optionally, in other embodiments, the light emitted from the lamp bead 45 may also be reflected to the swingable flame head 42 via a reflector. The lamp bead 45 may include at least two light emitting elements (not shown here), and the at least two light emitting elements change lights emitted therefrom to form the flickering effect. The specific structure of the lamp bead 45 is the same as that of the lamp bead 13 in the first embodiment of the electronic candle of the present disclosure, and will not be described in detailed any more.

Meanwhile, the lamp cap assembly 40 may further include a restricting ring 46 embedded in a top of the mounting base 41.

Figure 14:
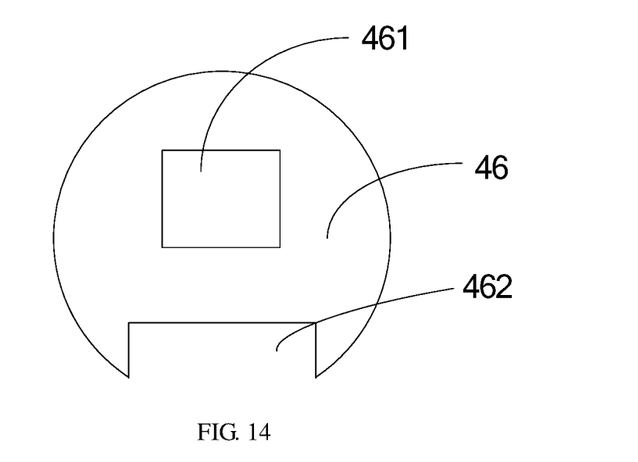
FIG. 14 is a structural view of a restricting ring of the second embodiment of the electronic candle of the present disclosure.

Referring to FIG. 14, a flame head slot 462 may be defined on one side of the restricting ring 46. The flame head slot 462 may restrict the swingable flame head 42 in the supporting portion 431 of the horizontal bar 43, and prevent the swingable flame head 42 from falling off. The swingable flame head 42 may pass through the flame head slot 462, and may be swung freely in the flame head slot 462 without restriction. The other side of the restricting ring 46 may be provided with a light slot 461, and the light emitted from the lamp bead 45 may be irradiated onto the swingable flame head 42 via the light slot 461.

It couis understood that, in other embodiments, the lamp cap assembly 40 may not contain the flame head support 47. That is, the lamp holder 44 and the horizontal bar 43 opposite to each other may be directly arranged on the inner wall of the mounting base 41.

Referring to FIG. 3, the base 20 may further include an electronic control device 27 located on an outer wall of the fragrance cavity 21. Optionally, a driving chip may be arranged in the electronic control device 27, and may be configured to control the switch-on and switch-off of the fan 31, and control the at least two light emitting elements in the lamp bead 45 to change the lights emitted therefrom to form the flickering effect.

Referring to FIG. 5, a toggle switch 28 may be arranged at a bottom surface of the base 20, and the toggle switch 28 may be connected to the electronic control device 27. When the toggle switch 28 is switched on, the electronic control device 27 may control the fan 31 to rotate, and control the at least two light emitting elements in the lamp bead 45 to emit light.

In the electronic candle described in the above embodiments, at least two light emitting elements may be arranged in a same lamp bead, and the fragrance cavity, the fan assembly and the swingable flame head may be provided. In this way, it is possible to save material and space, meanwhile the electronic candle may diffuse fragrance; the light emitted from the electronic candle may have a dynamic effect, and harmonious atmosphere may be created as a result.

The foregoing is merely embodiments of the present disclosure, and is not intended to limit the scope of the present disclosure. Any equivalent structure or flow transformation made based on the specification and the accompanying drawings of the present disclosure, or any direct or indirect applications of the disclosure on other related fields, shall all be covered within the protection of the present disclosure.

What is claimed is:

1. An electronic candle, comprising:
   at least one lamp bead having at least two light emitting elements provided therein; wherein the at least two light emitting elements change lights emitted therefrom to form a flickering effect;
   a lamp cap assembly comprising a mounting base, a flame head support and a swingable flame head;
   wherein the flame head support is fixedly connected to the mounting base; the swingable flame head is movably connected to the flame head support;
   a receiving space is defined in the flame head support; a lamp holder is embedded into an inner wall of the flame head support; the lamp bead is mounted in the lamp holder, and is located on one side of the swingable flame head; the lights emitted from the lamp bead is irradiated onto the swingable flame head, or reflected to the swingable flame head via a reflector;
   a horizontal through-hole is formed in the swingable flame head; a support pin is protruded from a top portion of the horizontal through-hole; the support pin is located in the center of gravity;
   a horizontal bar is formed on an inner wall of the flame head support that is opposite to the lamp holder; a recess is formed on a surface of the horizontal bar;
   the swingable flame head passes through the horizontal bar via the horizontal through-hole, and is supported in the recess via the support pin; components of the swingable flame head apart from the support pin are not in contact with the horizontal bar; when a breeze blows, the swingable flame head is swingable.

2. The electronic candle as described in claim 1, wherein the at least two light emitting elements each are light emitting diodes; the at least two light emitting elements change lights emitted therefrom wherein:
   emission colors of the lights emitted from at least one of the two light emitting elements are changed, in such a way that a relative emission color or an overall color of the lights emitted from the two light emitting elements is changed; or
   emission strength of the lights emitted from at least one of the two light emitting elements is changed, in such a way that relative emission strength or overall strength of the lights emitted from the two light emitting elements is changed.

3. The electronic candle as described in claim 1, further comprising:
   an electronic control device, connected to the at least two light emitting elements and configured to control the at least two light emitting elements to change lights emitted therefrom to form the flickering effect;
   wherein the at least two light emitting elements share at least one common lead wire to connect to the electronic control device; or
   when the lamp bead has N light emitting elements, (N+1) lead wires are used to connect the at least two light emitting elements to the electronic control device; wherein N is a positive integer larger than or equal to 2.

4. The electronic candle as described in claim 1, further comprising a main body; wherein a cavity is defined in the main body; a base is arranged in the cavity; the base comprises a fragrance cavity capable of diffusing fragrance to an outer side of the electronic candle.

5. The electronic candle as described in claim 4, wherein the base further comprises a bottom cover plate and a power supply cavity;

the power supply cavity is arranged on one side of the fragrance cavity; a stepped surface recessed downwardly is formed on a bottom surface of the base that corresponds to the fragrance cavity and the power supply cavity; at least one hole is defined in a position on the bottom cover plate that corresponds to the fragrance cavity; a fragrance element is arranged in the fragrance cavity; fragrance of the fragrance element in the fragrance cavity is diffused to the outer side of the electronic candle via the hole.

6. The electronic candle as described in claim 1, further comprising a main body, wherein a cavity is defined in the main body; a base and a fan assembly are arranged in the cavity; a blade is arranged at a bottom of the swingable flame head; the blade is rotatable under the action of the fan assembly, thereby driving the swingable flame head to swing.

7. The electronic candle as described in claim 6, wherein the base comprises a fragrance cavity;

the fan assembly comprises a fan and a fan base;

the fan base comprises a first cavity and a second cavity offset one another; the fan is mounted in the first cavity; wall of the first cavity is fixedly connected to the base, and an air exhausting surface of the fan is right opposite to the fragrance cavity; when the fan rotates, fragrance of the fragrance element in the fragrance cavity is diffused to the outer side of the electronic candle.

8. The electronic candle as described in claim 7, wherein the horizontal bar is T-shaped; the horizontal bar comprises a supporting portion and a restricting portion; the recess is formed in the supporting portion; a width of the supporting portion is smaller than a diameter of the horizontal through-hole, and a width of the restricting portion is larger than the diameter of the horizontal through-hole;

a positioning frame is formed in a position on the base that corresponds to an exit of the fragrance cavity; a plurality of positioning posts are arranged on the base on two sides of the positioning frame; a plurality of fixing lugs are arranged on an external wall of the first cavity of the fan base; wall of the first cavity is sleeved on an outer side of the positioning frame, and is fastened to the positioning posts via the plurality of fixing lugs;

the lamp cap assembly is sleeved on wall of the second cavity of the fan base via the mounting base; the lamp cap assembly further comprises a restricting ring embedded in a top of the mounting base; a flame head slot and a light slot are defined on the restricting ring; the swingable flame head passes through the flame head slot, and the lights emitted from the lamp bead are irradiated onto the swingable flame head via the light slot;

the lamp holder comprises a first portion and a second portion; at least one locking post and a first receiving space are provided on the first portion; at least one locking hole and a second receiving space are provided on the second portion; after the first portion and the second portion are locked together via the at least one locking post and the at least one locking hole, a third receiving space is formed by the first receiving space and the second receiving space, and the lamp bead is mounted in the third receiving space.

* * * * *